United States Patent [19]
Sato et al.

[11] Patent Number: 5,148,467
[45] Date of Patent: Sep. 15, 1992

[54] X-RAY SOURCE HOLDING APPARATUS

[75] Inventors: Hiroaki Sato; Syunichiro Nishigaki, both of Ootawara, Japan

[73] Assignee: Kabushiki Kaisha Toshiba, Kawasaki, Japan

[21] Appl. No.: 678,238

[22] Filed: Apr. 1, 1991

[30] Foreign Application Priority Data

Apr. 3, 1990 [JP] Japan .................. 2-87481

[51] Int. Cl.$^5$ ............................................. H05G 1/02
[52] U.S. Cl. .................................. 378/197; 378/193
[58] Field of Search ............... 378/197, 196, 195, 198, 378/193

[56] References Cited

U.S. PATENT DOCUMENTS 3,803,417  4/1974  Kok ...................... 378/197
4,759,048  7/1988  Ohlson ................... 378/197

Primary Examiner—Craig E. Church
Attorney, Agent, or Firm—Oblon, Spivak, McClelland, Maier & Neustadt

[57] ABSTRACT

An X-ray source holding apparatus comprises a rotatable plate, a holding unit and a control circuit. The rotatable plate is rotatably supports an X-ray source, and positioning holes are formed in the rotatable plate. The holding unit pivotally supports the rotating plate of the rotatable plate and contains a lock mechanism and a holding unit. The lock mechanism is made up of a lock pin which locks the rotatable plate by engagement with the positioning hole, and a spring which urges the lock pin toward the rotatable plate. The solenoid drives the lock mechanism such that the lock pin is disengaged from the positioning hole. The control circuit starts the driving of the lock mechanism in response to the operation of a control switch. Further, the control circuit controls the solenoid in such a way that the driving of the lock mechanism is stopped when a predetermined time has elapsed from the start of the driving of the lock mechanism.

20 Claims, 9 Drawing Sheets

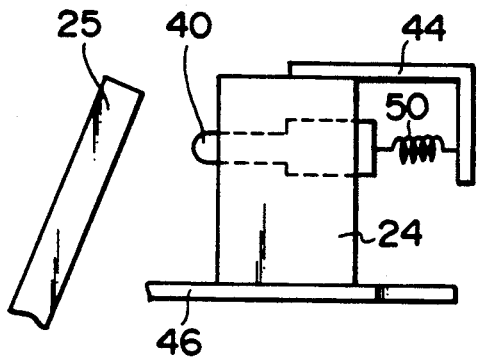
F I G. 11
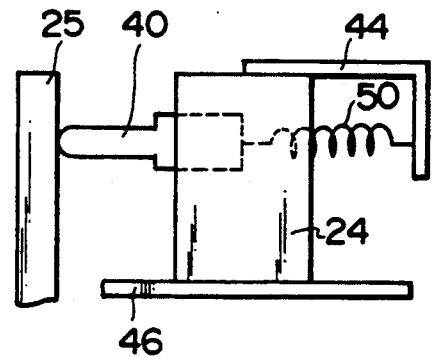
F I G. 12
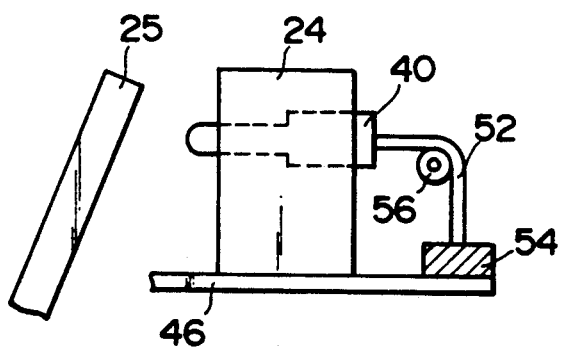
F I G. 13
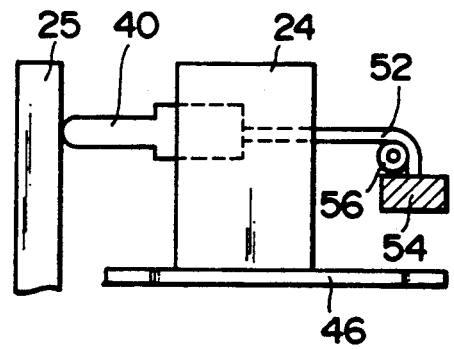
F I G. 14 ic system, a guide rail is installed on the ceiling, and a slider which is slidable along the guide rail is provided. A telescopic holding arm is suspended from the slider, and a holding unit incorporating an X-ray tube rotating mechanism is coupled to the lower end of the holding arm. A rotatable disk, which is rotatable around a horizontal axis parallel to the guide rail, is coupled to one face of the holding unit. A frame, on which an X-ray tube and a diaphragm device are supported, is attached to the rotatable plate.

X-RAY SOURCE HOLDING APPARATUS

BACKGROUND OF THE INVENTION

1. Field of the Invention

The present invention relates to an X-ray source holding apparatus which rotatably holds an X-ray tube such that the X-ray irradiation direction can be adjusted. More specifically, the present invention relates to an X-ray source holding apparatus which locks the posture of an X-ray tube, to thereby fix the X-ray irradiation direction.

2. Description of the Related Art

The X-ray source holding apparatus of the above type is incorporated in an X-ray diagnostic system, and is employed by an X-ray tube rotating mechanism which varies the posture of an X-ray tube, i.e., the X-ray irradiation direction.

An X-ray diagnostic system suspended from a ceiling is well known in the art. In this type of X-ray diagnost When the above X-ray diagnostic system is in use, it is necessary to change the X-ray irradiation direction (i.e., the posture of the X-ray tube) depending on the case where a subject is standing and the case where the subject is lying on an examination bed or the like. To change the X-ray irradiation direction, the rotatable disk is manually rotated around the horizontal axis and locked at one of positions determined beforehand. With the rotatable disk locked in this manner, X-rays are irradiated in a desirable direction.

To lock the rotatable disk at a desirable position, the rotatable disk has positioning holes formed therein, and the holding unit incorporates a lock mechanism. The lock mechanism is made up of a lock pin, and a spring which urges the lock pin to the rotatable disk and inserts it into one of the positioning holes. When the X-ray irradiation direction coincides with one of directions corresponding to the predetermined locking positions, the lock pin protrudes from the side face of the holding unit and is inserted into one of the positioning holes. As a result, the rotation of the rotatable disk is prohibited, and the X-ray irradiation direction is fixed.

To change the X-ray irradiation direction, the operator manually pulls the lock pin out of the positioning hole against the urging force of the spring, to thereby unlock the rotatable disk. Then, the operator manually rotates the rotatable disk to change the X-ray irradiation direction. If the operator wants to fix the X-ray irradiation direction, he or she further rotates the rotatable disk until the lock pin urged by the spring is inserted to another positioning hole. As is understood from this, the operator has to manually pull the lock pin out of the positioning hole and rotate the rotatable disk, when the operator wants to change the X-ray irradiation direction (i.e., the posture of the X-ray tube). Such manual operations are annoying to the operator.

In general, three positioning holes are formed in the circumferential regions of the rotatable disk such that they are shifted from each other by an angle of 90°. Let it be assumed that such a general type rotatable plate has to be rotated 180° from one locked position to another. In this case, the operator pulls the lock pin from the positioning hole and rotates the rotatable disk. When the disk has just been rotated 90°, the lock pin engages with the positioning hole 90° shifted from the first positioning hole. Thus, the operator pulls the lock pin out of the positioning hole once again, and further rotates the plate until the lock pin engages with the positioning hole 180° shifted from the first positioning hole. Obviously, this operation is troublesome to the operator. If the rotatable disk has four or more positioning holes, the operation is more troublesome since the operator has to repeatedly release the lock pin from the positioning holes during the rotation of the disk.

As has been described, the X-ray source holding apparatus incorporated in the above X-ray diagnostic system requires the operator to manually pull the lock pin from the positioning holes of the rotatable disk when the operator rotates the rotatable disk to change X-ray irradiation directions. Such a manual operation required for unlocking the rotatable disk is very troublesome to the operator.

SUMMARY OF THE INVENTION

Accordingly, an object of the present invention is to provide an X-ray source holding apparatus which permits a lock member to be released from a movable X-ray tube holding unit easily and reliably, i.e., allows easy and reliable unlocking of the movable X-ray tube holding unit when the holding unit is moved to change X-ray irradiation directions.

To achieve this object, the present invention provides an X-ray source holding apparatus, comprising: a holding unit which movably holds an X-ray source and has a positioning part; a lock mechanism for locking the X-ray source by engagement with the positioning part; unlock means for driving the lock mechanism to unlock the X-ray source; and control means for causing the unlock means to unlock the X-ray source during a predetermined period of time.

The present invention also provides an X-ray source holding apparatus, comprising: a holding unit which movably holds an X-ray source and has a positioning part; brake means for locking the X-ray source at an arbitrary position thereof; a lock mechanism for locking the X-ray source by engagement with the positioning part; unlock means for driving the lock mechanism to unlock the X-ray source; and control means for causing simultaneously the unlock means and the brake means to unlock the X-ray source, for causing the unlock means to unlock the X-ray source during a predetermined period of time.

The present invention further provides an X-ray source holding apparatus, comprising: a holding unit which movably holds an X-ray source and has a positioning part; a lock mechanism for locking the X-ray source by engagement with a positioning part; a rod-like link mechanism having a first end which is connected to the lock mechanism and a second end which is to be moved in a predetermined direction, said link mechanism disengaging the lock mechanism and the positioning part from each other, to thereby unlock the X-ray source, when the second end of the link mechanism is moved in said predetermined direction; unlock means for driving the lock mechanism to unlock the X-ray source, said unlock means including: an armature having a tip end which is adapted to push the second end of the link mechanism; and a solenoid for moving the armature toward the second end of the link mechanism; setting means for moving the armature to a position located away from the second end of the link mechanism; and control means for causing the unlock mean to unlock the X-ray source during a predetermined period of time.

According to the first X-ray source holding apparatus, the driving of the solenoid is started when the control switch is turned on. The solenoid pulls the lock pin from the positioning hole, so that the X-ray source is unlocked. When a predetermined time has elapsed from the operation of the control switch, the driving of the solenoid stops.

According to the second X-ray source holding apparatus, the driving of both the solenoid and the electromagnetic brake is started when the control switch is turned on, and the solenoid and the electromagnetic brake release the X-ray source from the locked state. When a predetermined time has elapsed from the time at which the X-ray source is unlocked from the lock pin, the driving of the solenoid stops.

According to the third X-ray source holding apparatus, the armature can be kept sufficiently away from the second end of the link mechanism when the armature does not drive that second end. When the armature is driven by the solenoid, it moves for a certain distance until it contacts the second end of the link mechanism. Therefore, the link mechanism can be rotated in a reliable manner.

As may be understood from the above, the rotatable disk, to which the X-ray source is connected, can be easily unlocked when any one of the first to third X-ray source holding apparatuses is employed.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 11 shows a solenoid and associated parts employed in a third embodiment of the present invention;

FIG. 12 shows the state where the solenoid shown in FIG. 11 is actuated;

FIG. 13 shows a solenoid and associated parts employed in a fourth embodiment of the present invention; and FIG. 14 shows the state where the solenoid shown in FIG. 13 is actuated.

DETAILED DESCRIPTION OF THE PREFERRED EMBODIMENTS

X-ray source holding apparatuses according to the embodiments of the present invention will no be described, with reference to the accompanying drawings.

FIGS. 1 through 7 show the first embodiment of the present invention. The X-ray source holding apparatus of this embodiment is employed in the overhead-suspended type X-ray diagnostic system shown in FIGS. 6 and 7.

Figure 1:
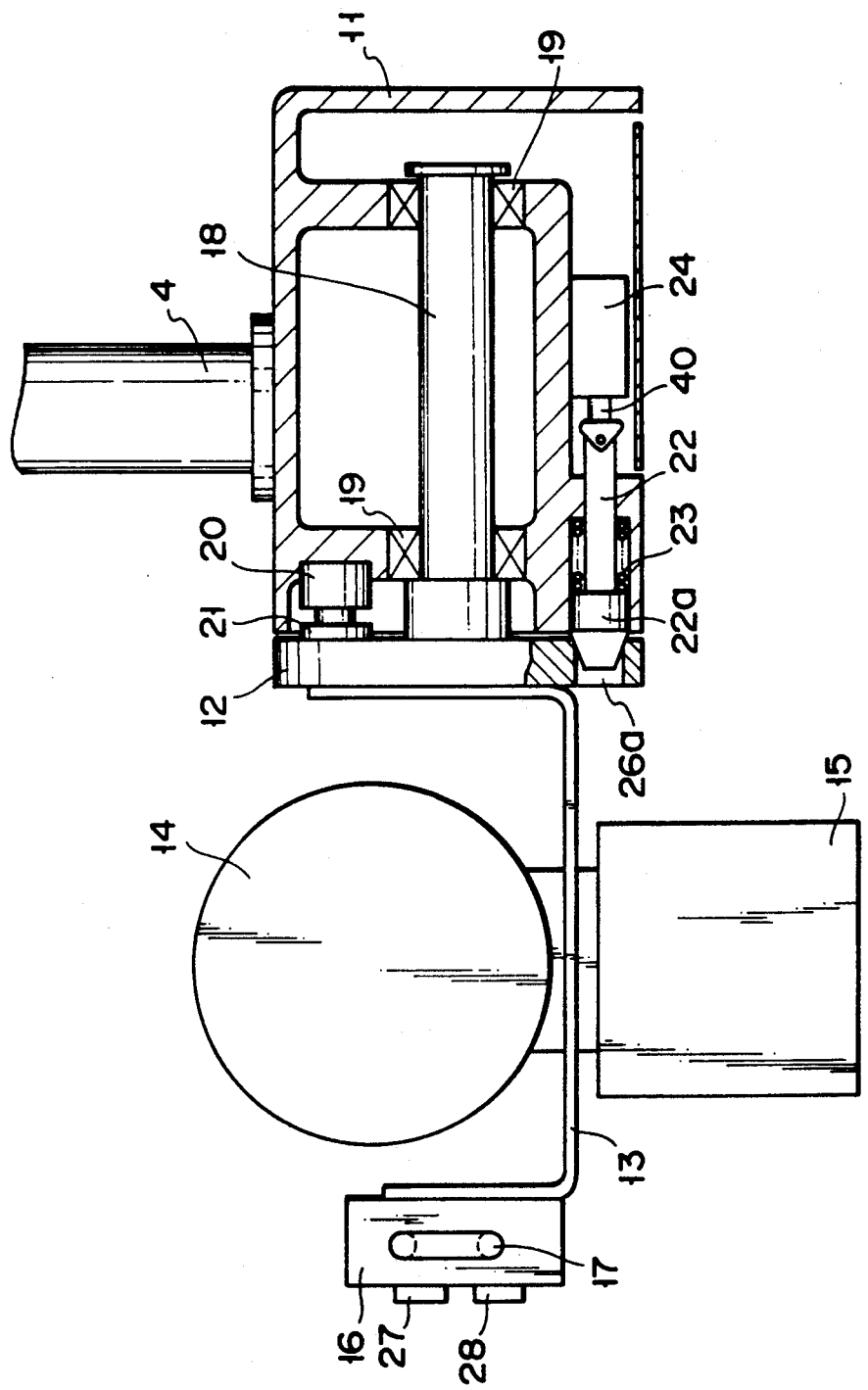
FIG. 1 is a sectional view of a holding unit incorporated in an overhead-suspended type X-ray diagnostic system according to a first embodiment of the present invention.
Figure 2:
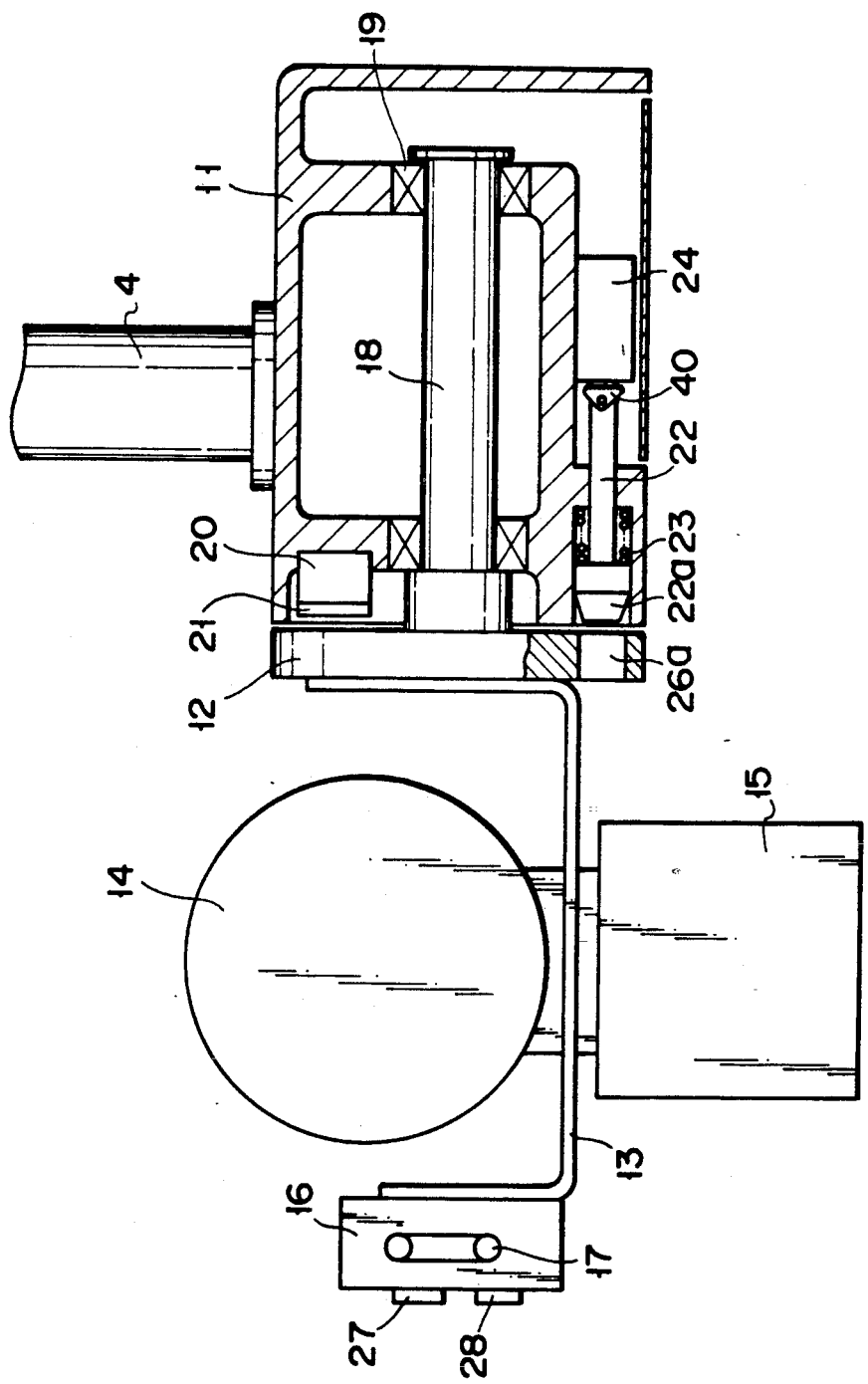
FIG. 2 is a sectional view illustrating the state where a rotatable plate is not locked by a lock pin of the holding unit shown in FIG. 1.

FIGS. 1 and 2 illustrate the structure of the X-ray source holding apparatus according to the first embodiment. In FIGS. 1 and 2, like reference numerals are used to denote like structural components shown in FIGS. 6 and 7.

Figure 6:
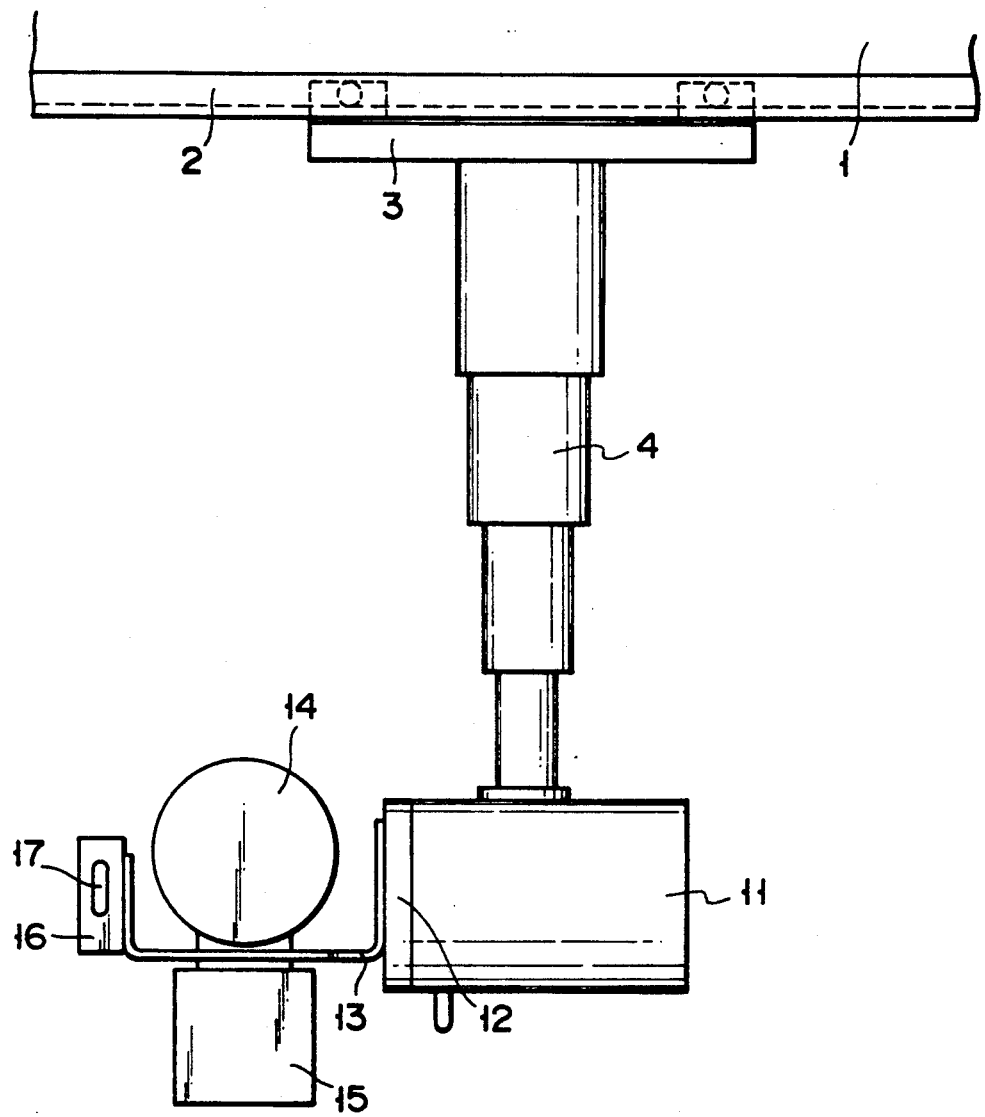
FIG. 6 is a schematic side view of the overhead-suspended type X-ray diagnostic system according to the first embodiment.
Figure 7:
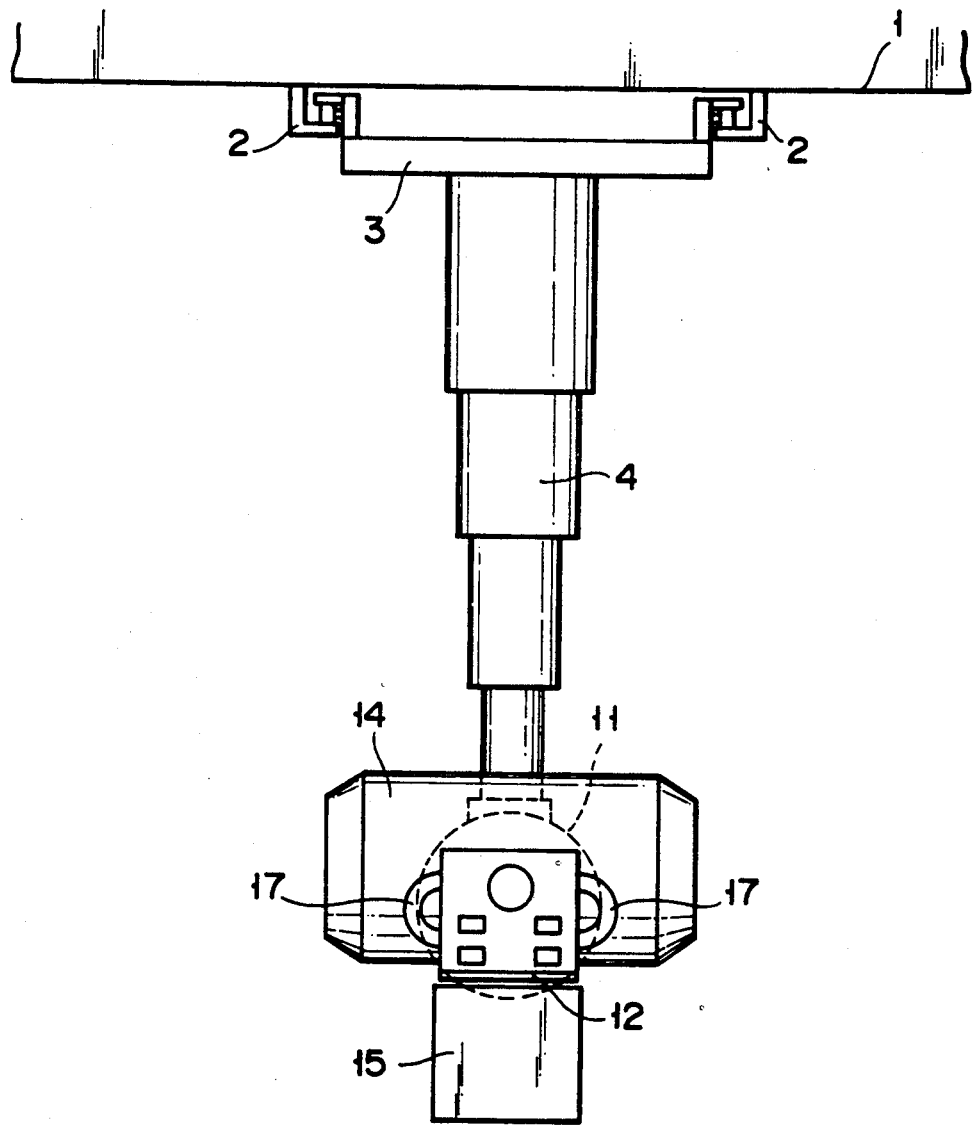
FIG. 7 is a schematic front view of the overhead-suspended type X-ray diagnostic system.

As is shown in FIGS. 6 and 7, a guide rail 2 is installed on a ceiling 1, and a slider 3 which is slidable along the rail 2 is provided at the ceiling 1. In the illustration shown in FIG. 6, the slider 3 can slide right and left. A telescopic holding arm 4 is suspended from the slider 3, and a holding unit is coupled to the lower end of the holding arm 4.

In the description below, that portion of the system which is depicted on the left side of FIG. 6 will be referred to as a front portion, while that portion which is depicted on the right side of FIG. 6 will be referred to as a rear portion.

The holding unit is comprised of a housing 11 horizontally attached to the lower end of the holding arm 4, a rotatable disk 12 which is provided on the front face of the housing 11 and is rotatable around a horizontal axis parallel to the guide rail 2, and a frame 13 which has a rear end attached to the rotatable plate 12 and on which an X-ray tube 14 and a diaphragm device 15 are supported. A control box 16 is attached to the front end of the frame 13. The control box 16 is provided with a switch which is operated to start or stop X-ray irradiation, and a handle 17 with which the X-ray irradiation direction is changed. To change the X-ray irradiation direction, the operator rotates the frame 13 while holding the handle 17. Since, therefore, the X-ray tube 14 is rotated with a rotation of the frame 13, the X-ray irradiation direction is changed, accordingly. It should be noted that the X-ray irradiation direction has to be changed depending on the case where an subject is standing during diagnosis and the case where the subject is lying. In order to meet this requirement, the X-ray tube 14 can be rotated around the horizontal axis and fixed at one of predetermined positions. With the X-ray tube 14 fixed at one of the positions, X-rays are irradiated to a desirable direction.

A description will now be given of the structure incorporated in the housing 11 of the holding unit.

As is shown in FIG. 1, a rotating shaft 18, which extends horizontally and is rotatably supported by bearings 19, is arranged inside the housing 11. The rotatable disk 12 mentioned above is attached to the front end of the rotating shaft 18. An electromagnetic brake 20 is arranged in the front region of the housing 11 and is located, for example, just above the rotating shaft 18. It should be noted that the electromagnetic brake 20 is not absolutely necessary to the present invention; the electromagnetic brake 20 is employed in the case where the rotatable disk 12 has to be locked at an arbitrary position in order to fix the X-ray irradiation direction arbitrarily. The electromagnetic brake 20 is made up of an electromagnet, a return spring, and a brake member 21. When the electromagnet is energized, it horizontally moves the brake member 21 toward the rotatable disk 12 and presses it against one side of the rotatable disk 12, thereby locking the rotatable disk 12. When, on the other hand, the electromagnet is de-energized, it is returned by the returned spring, allowing rotation of the rotatable disk 12. In this manner, the electromagnetic brake 20 locks or unlocks the rotatable disk 12.

A lock pin 22 is arranged in the front region of the housing 11 and is located, for example, just under the rotating shaft 18. The lock pin 22 is horizontally movable; in other words, it can be moved to the rotatable plate 12 or away from the rotatable plate 12. A tapered portion 22a, having a large diameter, is located at the tip end of the lock pin 22, and a compression coil spring 23 is inserted between the rear end face of the tapered portion 22a and the housing 11. By the compression coil spring 23, the lock pin 22 is urged toward the rotatable disk 12 at all times. A solenoid 24 is attached to the housing 11 on the rear side of the lock pin 22. The solenoid 24 is provided with an armature 40, and this armature 40 is connected to the rear end of the lock pin 22 by means of a pin. When actuated, the solenoid 24 pulls the armature 40 away from the rotatable plate 12.

A plurality of positioning holes, into each of which the tapered portion 22a of the lock pin 22 can be inserted, are formed in the peripheral portion of the rotatable disk 12. The locations of the positioning holes are determined in accordance with desirable directions in which the X-ray tube 14 irradiates X-rays. For example, three positioning holes 26a to 26c are formed in the manner shown in FIG. 3. As may be understood from FIG. 3, when the rotatable disk 12 is locked by utilization of positioning hole 26a, X-rays are irradiated in the direction indicated by arrow A in FIG. 3. When the rotatable disk 12 is locked by utilization of positioning hole 26b, X-rays are irradiated in the direction indicated by arrow C in FIG. 3. When the rotatable disk 12 is locked by utilization of positioning hole 26c, X-rays ar irradiated in the direction indicated by arrow B in FIG. 3.

Turning back to FIG. 1, the frame 13 mentioned above is attached to the front side of the rotatable disk 12, and supports the X-ray tube 14 and the diaphragm device 15 mounted thereon. The control box 16 is attached to the front end of the frame 13, and the handle 17 used for rotating the rotatable disk 12 is protruded from each side of the control box 16. A control switch 27, which is of e.g. a push button type, is provided on the front face of the control box 16, so as to operate the electromagnetic brake 20 arranged inside the housing 11. The control switch 27 is turned on when depressed and is turned off when freed. In addition to this control switch 27, a group of switches 28 necessary for carrying out X-ray diagnosis are provided on the front face of the control box 16.

Figure 4:
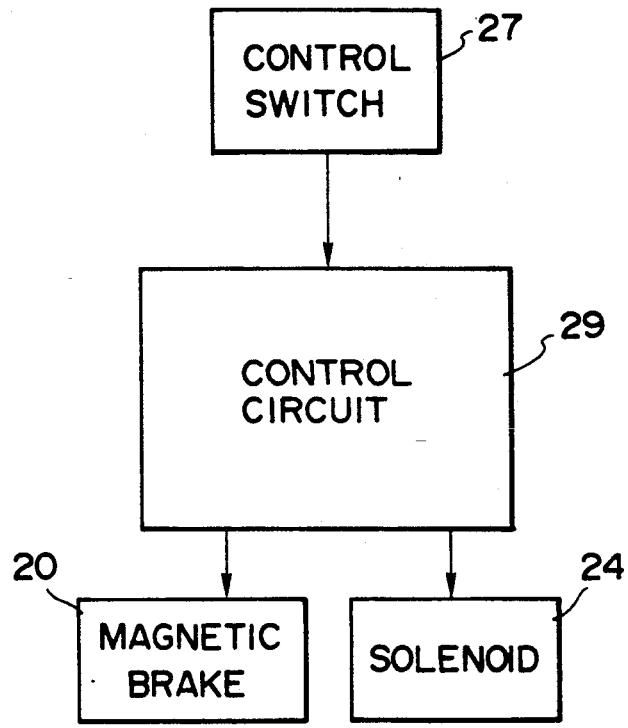
FIG. 4 is a block circuit diagram of a control device contained in the holding unit shown in FIG. 1.

A printed circuit board (not shown) having electronic components mounted thereon is arranged inside the control box 16. Circuits necessary for carrying out X-ray diagnosis are incorporated in the printed circuit board. In the first embodiment, the printed circuit board, as shown in FIG. 4, incorporates a control circuit 29. The control circuit 29 controls the times at which the driving of both the electromagnetic brake 20 and the solenoid 24 should be started or stopped, in accordance with the ON/OFF state of the switch 27. The control performed by the control circuit 29 will be described in more detail, with reference to FIG. 5 which shows the operating timings of the electromagnetic brake 20 and the solenoid 24.

In the case where the rotatable disk 12 is locked at one of the three positioning holes 26a to 26c and the operator thinks that the X-ray irradiation direction corresponding to that locked position is appropriate to the intended X-ray diagnosis, then the operator leaves the control switch 27 in the OFF state. When the control switch 27 is OFF, the control circuit 29 drives the electromagnetic brake 20, so that the electromagnetic brake 20 pushes the brake member 21 against the rotatable disk 12, to thereby apply a locking force to the rotatable disk 12. In the meantime, the solenoid 24 is kept unactuated. Thus, the compression coil spring 23 moves the lock pin 22 toward the rotatable disk 12, and the tapered portion 22a of the lock pin 22 is inserted into one of the positioning holes 26a to 26c formed in the rotatable disk 12.

Figure 5:
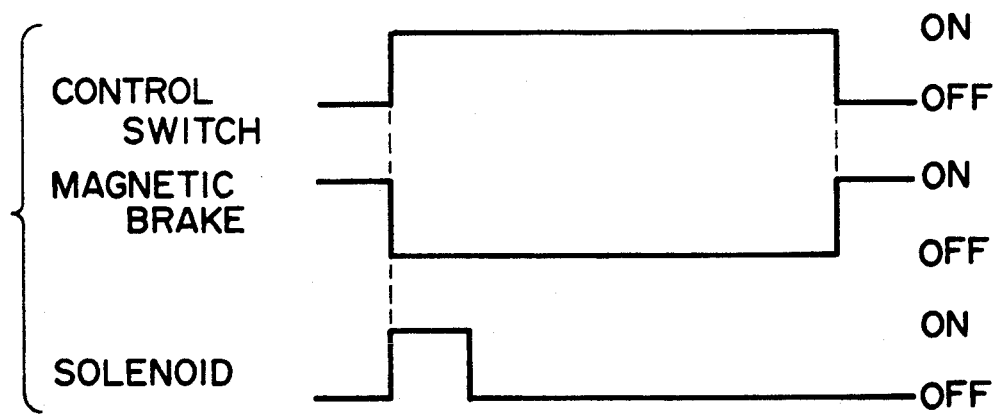
FIG. 5 is a timing chart showing the operating timings at which an electromagnetic brake and a solenoid are controlled by the control device shown in FIG. 4.

To unlock and rotate the rotatable disk 12, the operator depresses the control switch 27 to turn it on. In response to this, as shown in FIG. 5, the control circuit 29 stops the driving of the electromagnetic brake 20. Accordingly, the brake member 21 is separated from the rotatable disk 12 by the force of the return spring, to thereby release the rotatable disk 12 from the locked condition. Simultaneously, the control circuit 29 starts the driving of the solenoid 24. Accordingly, the solenoid 24 moves the lock pin 22 away from the rotatable disk 12 against the force of the compression coil spring 23. Since the tapered portion 22a is pulled out of the positioning hole, the rotatable disk 12 is released from the locked condition. When a predetermined time has elapsed from the time at which the electromagnetic brake 20 and the lock pin 22 unlock the rotatable disk 12, the control circuit 29 stops the driving of the solenoid 24. Thus, the compression coil spring 23 urges the lock pin 22 toward the rotatable disk 12. However, the positioning hole is deviated from the position of the lock pin 22 with the rotation of the rotating disk 12. Therefore, the portion where the positioning holes are not formed faces to the lock pin 22. In other words, the lock pin 22 is brought into a lock ready state, wherein its tapered portion 22a is ready for insertion into any one of the positioning holes 26a to 26c. When the rotatable disk 12 is rotated and one of the other positioning holes 26a to 26c comes to the position opposing to the lock pin 22, the tapered portion 22a of the lock pin 22 is inserted into the positioning hole, due to the urging force of the compression coil spring 23. The predetermined time mentioned above is a time during which the lock pin 22 is pulled out of the positioning hole and the rotatable disk 12 is rotated by the operator until the flat portion thereof (i.e., the portion where the positioning holes are not formed) opposes to the tapered portion 22a of the lock pin 22. Normally, the time is set to be about one second.

Next, a description will be given as to how the X-ray tube 14 is rotated and locked for fixing a desirable X-ray irradiation direction in the first embodiment.

Let it be assumed that the X-ray tube 14 is rotated from the position corresponding to X-ray irradiation direction A to the position corresponding to X-ray irradiation direction B. In this case, the operator unlocks the rotatable disk 12 and rotates it. To be more specific, the operator depresses the control switch 27 of the control box 16 to turn it on. In response to this operation, the control circuit 29 performs the following control. As is understood from FIG. 5, the driving of the electromagnet of the electromagnetic brake 20 is stopped when the control switch 27 is turned on, and the brake member 21 is moved away from the rotatable disk 12, due to the force of the return spring. As a result, the rotatable disk 12 is unlocked from the brake member 21. Simultaneously, the control circuit 29 starts the driving of the solenoid 24. Accordingly, the solenoid 24 moves the lock pin 22 away from the rotatable disk 12 against the force of the compression coil spring 23, and the tapered portion 22a of the lock pin 22 is pulled out of positioning hole 26a. Since the rotatable disk 12 is unlocked from the lock pin 22, the rotatable disk 12 is kept in a freely-rotatable condition.

As mentioned above, the rotatable disk 12 is unlocked from both the electromagnetic brake 20 and the lock pin 22, when the control switch 27 of the control box 16 is depressed.

Then, the operator rotates the rotatable disk 12 90° by holding the handle 17 of the control box 16, such that the X-ray tube 14 is moved from the position corresponding to X-ray irradiation direction A to the position corresponding to X-ray irradiation direction B. About one second after the start of the rotation of the rotatable disk 12 (more precisely, after the time at which the rotatable disk 12 is unlocked from both the electromagnetic brake 7 and the lock pin 22), the driving of the solenoid 24 is stopped by the control circuit 29. Therefore, the compression coil spring 23 urges the lock pin 22 toward the rotatable disk 12. In other words, the lock pin 22 is brought into a lock ready state wherein its tapered portion 22a is ready for insertion into any one of the positioning holes 26a to 26c. This being so, when positioning hole 26b comes to the position opposing to the lock pin 22, in place of positioning hole 26a, the tapered portion 22a of the lock pin 22 is inserted into positioning hole 26b, to thereby lock the rotatable disk 12. In this manner, the rotatable disk 12 is positioned and locked by utilization of positioning hole 26b, with the result that the X-ray tube 14 is reliably locked at the position corresponding to X-ray irradiation direction B.

As mentioned above, when the predetermined time has elapsed from the time when the rotatable plate 12 is unlocked from both the electromagnetic brake 20 and the lock pin 22, the control circuit 29 stops the driving of the solenoid 24, to thereby bring the lock pin 22 into a lock ready state. Therefore, the rotatable disk 12 reliably stops at the position corresponding to the desirable X-ray irradiation direction. When the rotatable disk 12 stops at that position, the operator frees the control switch 27 to turn it off. Accordingly, the driving of the electromagnetic brake 20 is started, and the brake member 21 locks the rotatable disk 12 once again.

X-ray irradiation directions A to C are directions which are frequency utilized during X-ray diagnosis. Therefore, these X-ray irradiation directions can be fixed by a combination of the lock pin 22 and positioning holes 26a to 26c. If the operator wants to fix the X-ray irradiation direction between directions A to C and directions A to B, then he or she frees the control switch 27 to turn it off. In response to this operation, the driving of the electromagnetic brake 20 is started, and the brake member 21 locks the rotatable disk 12.

In the first embodiment, the lock pin 22 need not be actuated by the solenoid 24 mentioned above; it may be actuated by any type of actuating member. In addition, the X-ray source holding apparatus of the first embodiment need not be a type wherein the X-ray tube 14 is rotated, but may be a type wherein the X-ray tube 14 is slid.

As has been described, according to the X-ray source holding apparatus of the first embodiment, the solenoid 24 unlocks the rotatable disk 12 by pulling out the lock pin 22 from the disk 12 in response to the operation of the control switch 27, without requiring any manual operation. In addition, since the electromagnetic brake 20 is employed, the X-ray irradiation direction of the X-ray tube 14 can be fixed arbitrarily, without being restricted by the locations of the positioning holes formed in the rotatable disk 12. Further, since the rotatable disk 12 can be unlocked with regards to the electromagnetic brake 20 and the lock pin 22 by depressing the control switch 27, it is easy to change the posture of the X-ray tube 14 from one position to another. Moreover, even when the rotatable disk 12 is unlocked with regards to both the electromagnetic brake 20 and the lock pin 22, the control circuit 29 automatically stops the driving of the solenoid 24 and brings the lock pin 22 into a lock ready state after the lapse of a predetermined time. Thus, the X-ray tube 14 can be reliably fixed in any desirable direction.

The X-ray source apparatus according to the second embodiment of the present invention will now be described. In the second embodiment, the driving force of the solenoid 24 is not directly transmitted to the lock pin 22, as it is in the first embodiment. In order to transmit a force greater than that driving force to the lock pin 22, a link 25 is employed between the solenoid 24 and the lock pin 22. Since the second embodiment is similar to the first embodiment except for the structure incorporated in the housing, only the structure incorporated in the housing will be described below.

Figure 8:
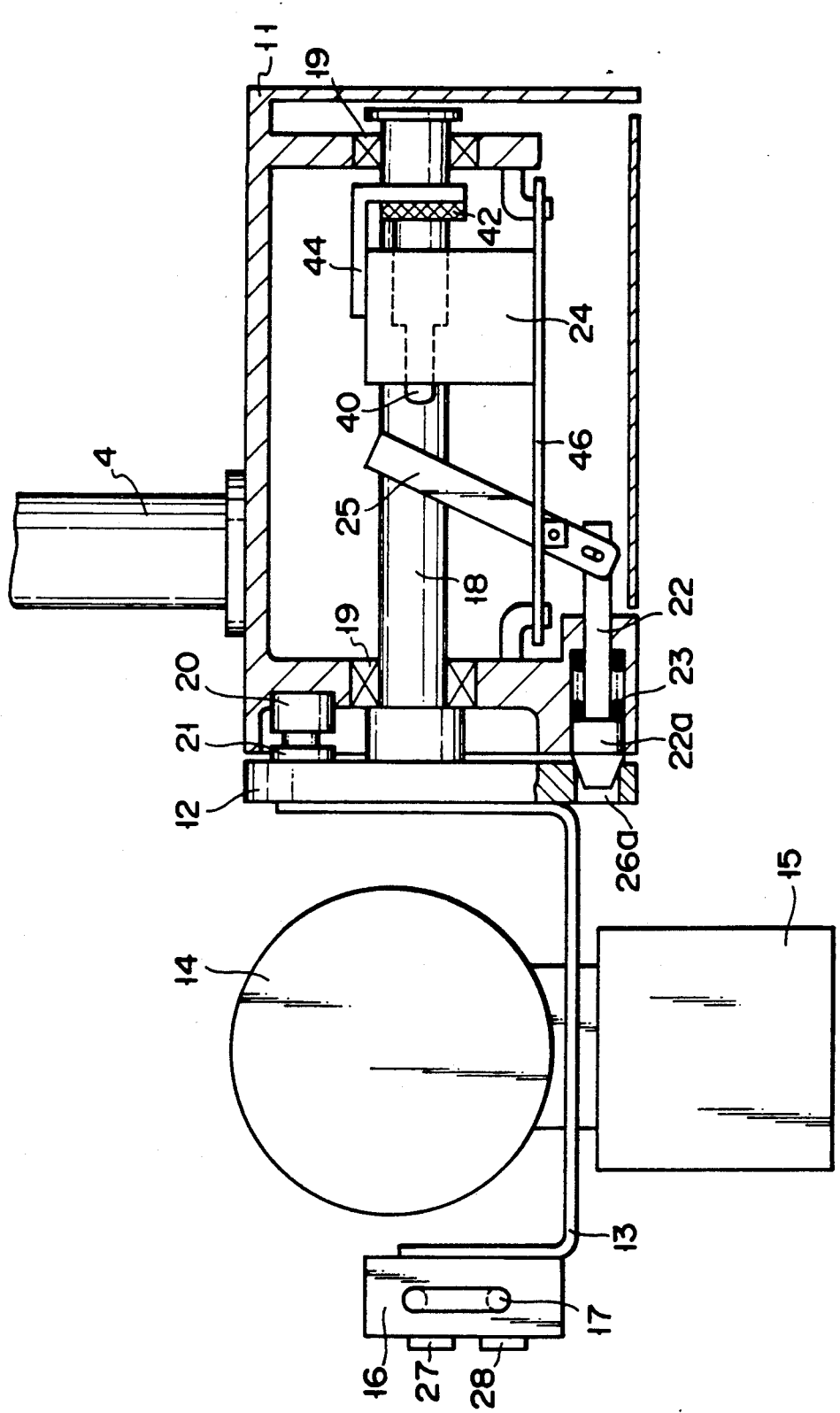
FIG. 8 is a sectional view of a holding unit incorporated in an overhead-suspended type X-ray diagnostic system according to a second embodiment of the present invention.

The structure incorporated in the housing will be detailed, with reference to FIG. 8. In the description below, that portion of the system which is depicted on the left side of FIG. 8 will be referred to as a front portion, while that portion which is depicted on the right side of FIG. 8 will be referred to as a rear portion. Inside the housing 11, a rotating shaft 18, which extends horizontally and is rotatably supported by bearings 19, is arranged. A circular rotatable disk 12 is attached to the front end of the rotating shaft 18. An electromagnetic brake 20 is arranged in the front region of the housing 11 and is located, for example, just above the rotating shaft 18. The electromagnetic brake 20 is made up of an electromagnet, a return spring, and a brake member 21. When the electromagnet is energized, it horizontally moves the brake member 21 toward the rotatable disk 12 and presses it against one side of the rotatable disk 12. When, on the other hand, the electromagnet is de-energized, it is returned by the returned spring, allowing rotation of the rotatable disk 12. In this manner, the electromagnetic brake 20 locks or unlocks the rotatable disk 12.

A lock pin 22 is arranged in the front region of the housing 11 and is located, for example, just under the rotating shaft 18. The lock pin 22 is horizontally movable; in other words, it can be moved to the rotatable disk 12 or away from the rotatable disk 12. A tapered portion 22a, having a large diameter, is located at the tip end of the lock pin 22, and a compression coil spring 23 is inserted between the rear end face of the tapered portion 22a and the housing 11. By the compression coil spring 23, the lock pin 22 is constantly urged toward the rotatable disk 12 and is projected from the housing 11. The rear end of the lock pin 22 is connected to one end of the link 25.

Figure 9:
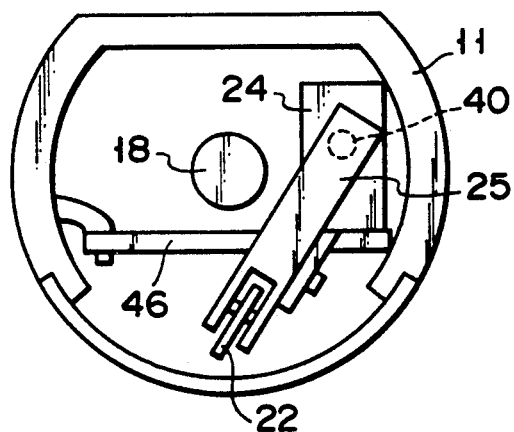
FIG. 9 illustrates the internal structure of the holding unit shown in FIG. 8.

FIG. 9 shows how the interior of the housing 11 looks like when viewed from the rotatable disk 12. As is shown in FIG. 9, the link 25 is arranged slantwise, so as not to prevent the movement of the rotating shaft 18, and the rear end of the lock pin 22 is shaped like a plate and is arranged slantwise. The link 25 is pivotally supported by a horizontal base plate 46 held by the housing 11. The one end of the link 25 has an hole, and a pin projected from the rear end of the lock pin 22 is inserted into the hole of the link 25. With this structure, the rotating movement of the link 25 (which is rotated, with the pivotal support point as a center) is transmitted to the lock pin 22 as a linear movement. When the link 25 is rotated counterclockwise, as viewed in FIG. 8, the lock pin 22 is moved rightward against the urging force of the coil spring 23.

Figure 10:
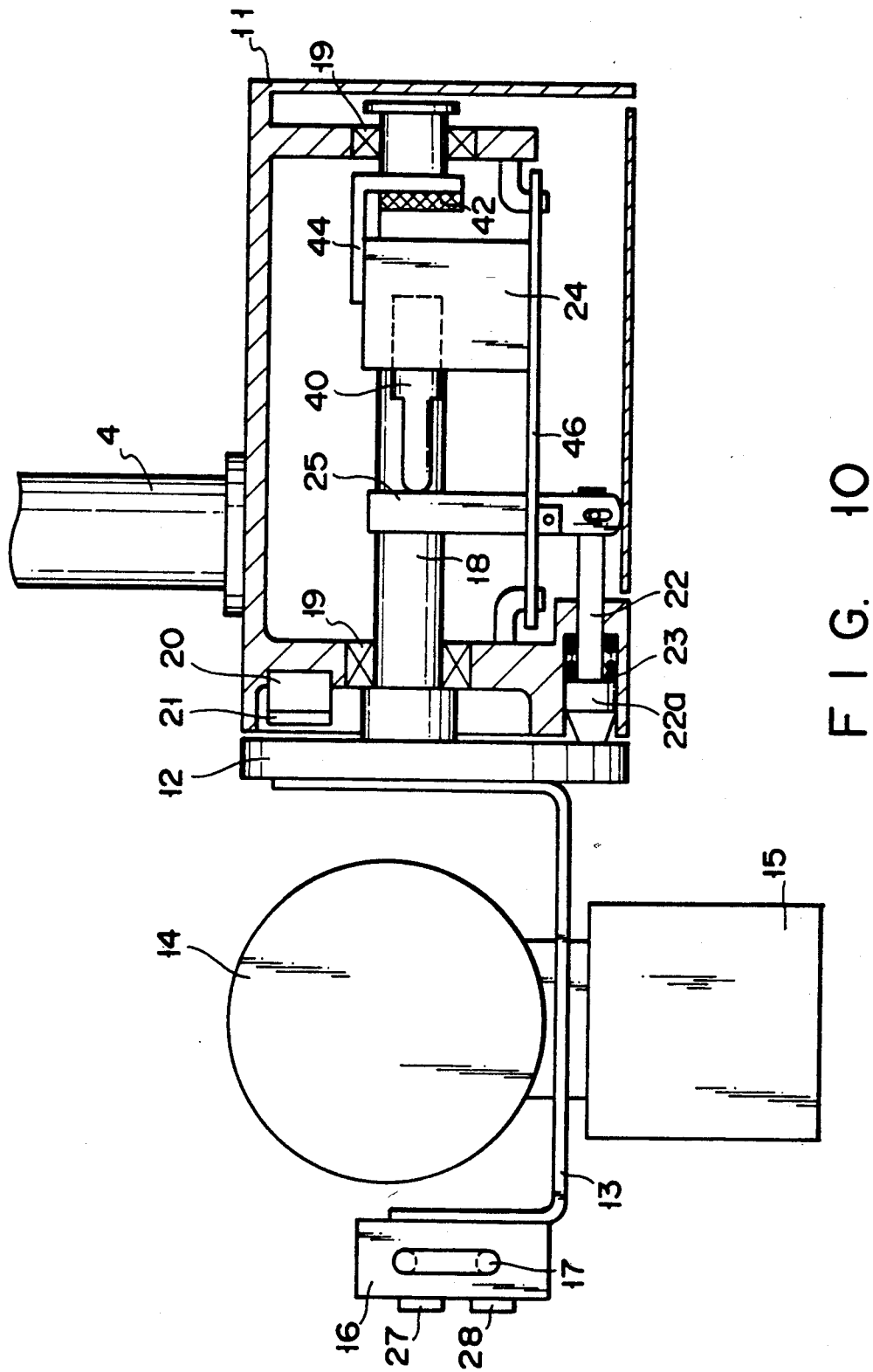
FIG. 10 is a sectional view illustrating the state where a rotatable plate is not locked by a lock pin of the holding unit shown in FIG. 8.

The solenoid 24 is mounted on the base plate 46 such that it is located on the rear side of the link 25. When energized, the solenoid 24 pushes an armature 40 leftward, thus rotating the link 25 counterclockwise, as is shown in FIG. 10. Since the force produced by the solenoid 24 is not very strong, the pivotal support point of the link 25 is closer to the lock pin 22 than the longitudinal center thereof. Thus, the force with which the link 25 drives the lock pin 22 is greater than the force with the link 25 is rotated by the armature 40.

The other end of the link 25 may be connected to the armature 40 in a similar manner to that in which it is connected to the lock pin 22. However, in the case where the link 25 is not connected to the armature 40, as in the second embodiment, it is possible to make the most of the driving force of the solenoid 24. The reason is that the armature 40 can move for a long distance until it contacts the link 25, and can therefore strike against the link 25 with great force.

When the solenoid 24 is not energized, the armature 40 is in a free state. Since, at the time, the lock pin 22 is urged by the coil spring 23 and is projected from the housing 11, the link 25 is rotated clockwise, as viewed in FIG. 8. Accordingly, the link 25 pushes the armature 40 rightward. To provide a limit to this movement of the armature 40, a stopper 44 is provided on the rear side of the solenoid 24. Further, a magnet 42 is provided on that side of the stopper 44 which faces the armature 40.

This magnet 42 attracts the armature 40, when the solenoid 34 is not energized and the armature 40 is therefore in a free state. The position to which the armature 40 is moved by the attraction force of the magnet 42 is the movement start position. It should be noted that the magnetic intensity of the magnet 42 is so determined as not to prevent the leftward movement of the armature 40 when the solenoid 24 is energized. When the solenoid 24 is de-energized, the armature 40 is moved rightward by the link 25 and is attracted by the magnetic intensity of the magnet 42 until it comes to the movement start position. When the armature 40 is at the movement start position, its tip end is located sufficiently away from the link 25. When the solenoid 24 is energized, the armature strikes against the link after moving for a sufficiently long distance. Since, therefore, the link 25 is pushed with great force, it is rotated counterclockwise, pushing the lock pin 22 rightward against the urging force of the coil spring 23.

Let us consider what will happen if no magnet is employed in the second embodiment. In this case, the armature 40 stops its rightward movement, with its tip end being in contact with the link 25 or in the vicinity of the link 25, when the solenoid 24 is de-energized. When the solenoid 24 is energized next, the armature 40 strikes against the link 25 without moving for a long distance. It is therefore likely that the armature 40 will not provide a sufficient impact for the link 25. In some cases, the lock pin 22 may not be pulled out of the positioning hole formed in the rotatable disk 12.

As in the first embodiment, a control box 16 is attached to the front end of a frame 13, and a handle 17 used for rotating the rotatable disk 12 is protruded from each side of the control box 16. A control switch 27, which is of e.g. a push button type, is provided on the front face of the control box 16, so as to operate the electromagnetic brake 20 arranged inside the housing 11. The control switch 27 is turned on when depressed and is turned off when freed. In addition to this control switch 27, a group of switches 28 necessary for carrying out X-ray diagnostic are provided on the front face of the control box 16.

A printed circuit board (not shown) having electronic components mounted thereon is arranged inside the control box 16. The circuits necessary for carrying out X-ray diagnostic are incorporated in the printed circuit board. For example, the printed circuit board incorporates a control circuit 29. This control circuit 29 controls the times at which the driving of both the electromagnetic brake 20 and the solenoid 24 should be started or stopped, in response to the operation of the control switch 27. Since the control performed by the control circuit 29 is similar to that of the first embodiment, a further description thereof will be omitted.

Next, a description will be given as to how the X-ray tube 14 is rotated and locked for fixing a desirable X-ray irradiation direction in the second embodiment.

Figure 3:
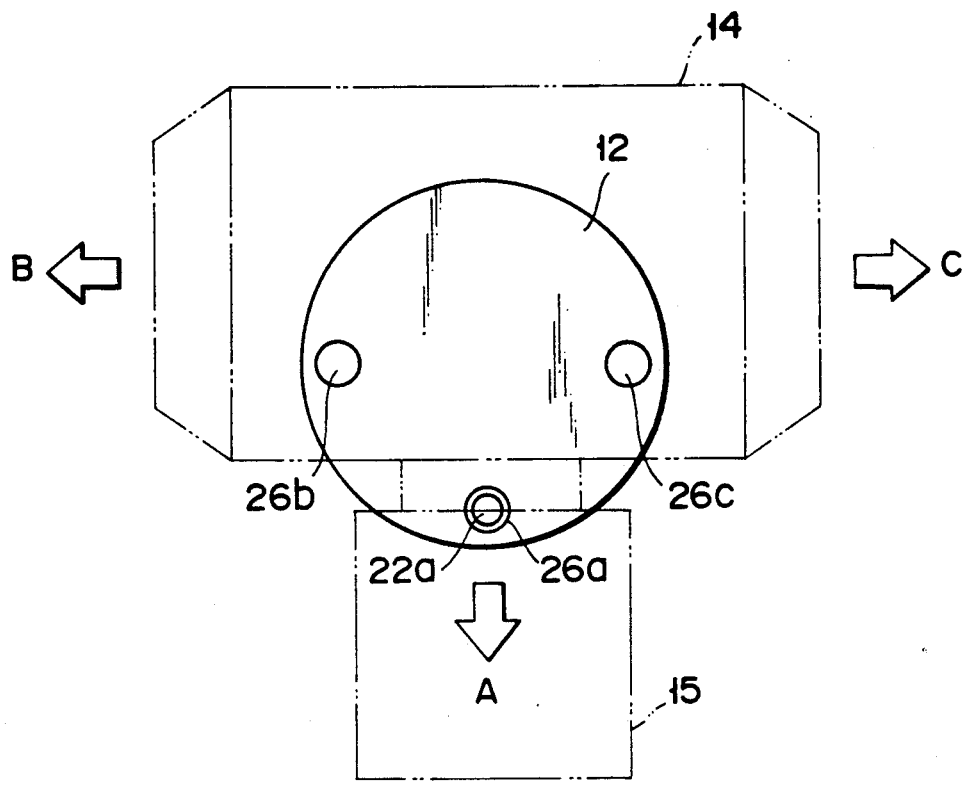
FIG. 3 shows relationships between the X-ray irradiation direction and the positions of positioning holes in the holding unit shown in FIG. 1.

Let it be assumed that the X-ray tube 14 is at the position corresponding to X-ray irradiation direction A (in which X-rays are irradiated downward, as viewed in FIG. 3). In this case, positioning hole 26a of the rotatable disk 12 opposites in position to the lock pin 22 protruded from the housing 11. As long as the control switch 27 of the control box 16 is not operated, the control circuit 29 drives the electromagnetic brake 20 in the manner shown in FIG. 8. That is, the electromagnetic brake 20 pushes the brake member 21 against the rotatable disk 12, to thereby apply a braking force to the rotatable disk 12. Since, at the time, the solenoid 24 is not driven, the compression coil spring 23 urges the lock pin 22 against the rotatable disk 12, and the tapered portion 22a of the lock pin 22 is inserted into positioning hole 26a. Accordingly, the rotating disk 12 is locked, and the X-ray tube 14 connected to the rotating disk 12 is also locked. In this manner, X-ray irradiation direction A is fixed.

Let it be assumed that the X-ray tube 14 is rotated from the position corresponding to X-ray irradiation direction A to the position corresponding to X-ray irradiation direction B. In this case, the operator unlocks the rotatable disk 12 and rotates it. To be more specific, the operator depresses the control switch 27 of the control box 16 to turn it on. In response to this operation, the driving of the electromagnet of the electromagnetic brake 20 is stopped, and the brake member 21 is moved away from the rotatable disk 12, due to the force of the return spring. As a result, the rotatable disk 12 is unlocked from the brake member 21. Simultaneous with the de-energization of the electromagnetic brake 20, the solenoid 24 is energized. Accordingly, the armature 40 moves leftward from the movement start position (at which the armature 40 has been kept by the magnet 42), and strikes against the link 25 with great force. Thus, the link 25 is rotated counterclockwise. As mentioned above, the armature 40 starts its leftward movement from a position sufficiently away from the link 25 and moves for a long distance before striking against the ink 25. Therefore, the force with which the link 25 is rotated is strong enough to pull the lock pin 22 against the force of the coil spring 23. As a result, the lock pin 22 is moved away from the rotatable disk 12, and the tapered portion 22a of the lock pin 22 is reliably pulled out of positioning hole 26a. In this manner, the rotating disk 12 is unlocked from the lock pin 22, and the rotatable disk 12 is set into a freely-rotatable condition.

Then, the operator rotates the rotatable disk 12 90° by holding the handle 17 of the control box 16, such that the X-ray tube 14 is moved from the position corresponding to X-ray irradiation direction A to the position corresponding to X-ray irradiation direction B. Since the control switch 27 is kept ON when the rotatable disk 12 is being rotated, the electromagnetic brake 20 is not driven, and the rotatable disk 12 is kept unlocked. After the lapse of a predetermined time (e.g., about one second) from the operation of the control switch 27 (during the time interval the rotation of the rotatable disk 12 is started), the driving of the solenoid 24 is stopped under the control of the control circuit 29. Therefore, the lock pin 22 is projected toward the rotatable disk 12, being urged by the compression coil spring 23. In other words, the lock pin 22 is set into a lock ready state, wherein its tapered portion 22a is projected to the flat portion of the rotatable disk 12. Until then, the rotatable disk 12 is rotated until the flat portion other than positioning hole 26a opposites in position to the lock pin 22. Since the lock pin 22 is pressed against the flat portion of the rotatable disk 12, the rotatable disk 12 can be rotated until the next positioning hole 26b opposites in position to the lock pin 22.

When the next positioning hole 26b comes to the position corresponding to the lock pin 22, the tapered portion 22a of the lock pin 22 is inserted into the positioning hole 26b, due to the spring force of the compression coil spring 23. As a result, the rotatable disk 12 is locked. In this manner, the rotatable disk 12 can be positioned and locked at the position corresponding to X-ray irradiation direction B. Accordingly, the X-ray tube 14 is reliably locked at the position corresponding to X-ray irradiation direction B.

As mentioned above, when the predetermined time has elapsed from the time when the rotatable disk 12 is unlocked from both the electromagnetic brake 20 and the lock pin 22, the control circuit 29 stops the driving of the solenoid 24 to thereby bring the lock pin 22 into a lock ready state. Therefore, the rotatable disk 12 reliably stops at the position corresponding to X-ray irradiation direction B. When the rotatable disk 12 stops at that position, the operator frees the control switch 27 turn it off. Accordingly, the driving of the electromagnetic brake 20 is started, and the brake member 21 locks the rotatable disk 12.

X-ray irradiation directions A–C are directions which are frequency utilized during X-ray diagnostic. Therefore, these X-ray irradiation directions can be fixed by a combination of the lock pin 22 and positioning holes 26a to 26c. If the operator wants to fix the X-ray irradiation direction between directions A to C, then he or she rotates the rotatable disk 12 to the position corresponding to the desirable X-ray irradiation direction and frees the control switch 2 to turn it off. In response to this operation, the driving of the electromagnetic brake 20 is started and the brake member 21 locks the rotatable disk 12.

In the second embodiment mentioned above, the driving force of the solenoid 24 is transmitted to the lock pin 22 after it is increased by utilization of the rotation of the link 25. In addition, the magnet 42 located behind the solenoid 24 attracts the armature 40 when the solenoid 24 is not energized, such that the armature 40 is located sufficiently away from the link 25. When the solenoid 24 is energized, the armature 40 strikes against the link 25 with great force, thus rotating the link 25. Since the link 25 is rotated with great force, the lock pin 22 is pulled reliably from a positioning hole 26, thus unlocking the rotatable disk 12.

FIG. 11 shows the solenoid and associated parts employed in the third embodiment of the present invention. In the third embodiment, the rear end of an armature 40 is connected to a stopper 44 by means of a coil spring 50, and the armature 40 is constantly pulled by the coil spring 50. When the solenoid 24 is not energized, the armature 40, which is then in a free state, is pulled by the coil spring 50 and is kept sufficiently away from the link 25, as is shown in FIG. 11. When the solenoid 24 is energized, the armature 40 moves leftward against the pulling force of the coil spring 50, thereby rotating the link 25 counterclockwise. As long as the pulling force of the coil spring 50 is so determined as not to adversely affect the movement of the armature 40, the third embodiment produces substantially the same advantages as the second embodiment.

FIG. 13 shows the solenoid and associated parts employed in the fourth embodiment of the present invention. In the fourth embodiment, the rear end of an armature 40 is connected to a weight 54 by means of a wire 52. The wire 52 is wound around a pulley 56, and the armature 40 is constantly pulled by the weight 54. When the solenoid 24 is not energized, the armature 40, which is then in a free state, is pulled by the weight 54 and is kept sufficiently away from the link 25, as is shown in FIG. 13. When the solenoid 24 is energized, the armature 40 moves leftward against the pulling force of the weight 54, thereby rotating the link 25 counterclockwise. As long as the weight 54 is so selected as not to adversely affect the movement of the armature 40, the fourth embodiment produces substantially the same advantages as the second embodiment.

The present invention is not limited to the above embodiments; it can be embodied or modified in various manners without departing from the spirit and scope of the invention. For example, the means for sufficiently isolating the armature 40 from the link 25 when the solenoid 24 is not energized is not limited to the magnet, the spring or the weight, as in the foregoing embodiments. If the armature 40 is supplied with a current flowing in the backward direction just before the solenoid 25 is energized to move the armature 40 to the link 25, it moves to a position sufficiently away from the link 25. When the solenoid 25 is energized, with the armature 40 at that position, then the armature 40 strikes against the link 25 with great force, thus strongly rotating the link 25. Accordingly, the lock pin 22 can be reliably pulled from the positioning hole. Moreover, the present invention is applicable not only to an X-ray diagnostic system wherein an X-ray tube is rotated, but also to an X-ray diagnostic system wherein an X-ray tube is slid.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. An X-ray source holding apparatus, comprising:
  a holding unit which movably holds an X-ray source;
  a lock mechanism for inhibiting the movement of said X-ray source; unlock means for disengaging said lock mechanism so as to allow the movement of said X-ray source; and
  control means for energizing said unlock means during a predetermined period of time upon reception of a command which is externally supplied.

2. An X-ray source holding apparatus according to claim 1, wherein:
  said X-ray source is provided with one of said positioning parts to inhibit the movement of said X-ray source, and a spring for urging the lock pin toward said movable member; and
  said unlock means drives said lock pin such that said lock pin is disengaged from one of said positioning parts against an urging force of said spring, thereby allowing the movement of said X-ray source.

3. An X-ray source holding apparatus according to claim 2, wherein:
  said holding unit rotatably holds the X-ray source;
  said lock mechanism inhibits the rotation of said X-ray source;
  said unlock means disengages said lock mechanism so as to allow the rotation of said X-ray source; and
  said movable member includes a rotatable member.

4. An X-ray source holding apparatus according to claim 3, wherein said unlock means includes an armature having one end connected to said lock pin for moving said lock pin away from said rotatable member, and a solenoid for driving said armature.

5. An X-ray source holding apparatus according to claim 4, wherein said unlock means further includes a rod-like link mechanism having a first end which is connected to said lock pin and a second end which is to be pushed by said solenoid, said link mechanism disengaging said lock pin from one of said positioning parts, to thereby allow the movement of said X-ray source, when said second end of said link mechanism is pushed by said solenoid.

6. An X-ray source holding apparatus according to claim 2, further comprising:
  a brake means for locking said X-ray source at an arbitrary position thereof, said control means causing said brake means to unlock said X-ray source upon reception of a command which is externally supplied.

7. An X-ray source holding apparatus according to claim 6, wherein said brake means includes an electromagnetic brake.

8. An X-ray source holding apparatus, comprising:
  a holding unit which movably holds an X-ray source;
  brake means for locking said X-ray source at an arbitrary position thereof;
  a lock mechanism for inhibiting the movement of said X-ray source;
  unlock means for disengaging said lock mechanism so as to allow the movement of said X-ray source; and
  control means for causing simultaneously said unlock means and said brake means to unlock said X-ray source, for energizing said unlock means during a predetermined period of time upon reception of a command which is externally supplied.

9. An X-ray source holding apparatus according to claim 5, wherein:
  said X-ray source is provided on a movable member having positioning parts;
  said lock mechanism includes a lock pin engageable with one of said positioning parts to inhibit the movement of said X-ray source, and a spring for urging said lock pin toward said movable member; and
  said unlock means drives said lock pin such that said lock pin is disengaged from one of said positioning parts against an urging force of said spring, thereby allowing the movement of said X-ray source, said lock pin and one of said positioning parts engaging with each other when said unlock means does not drive said lock pin, thereby inhibiting the movement of said X-ray source.

10. An X-ray source holding apparatus according to claim 9, wherein said unlock means includes an armature having one end connected to said lock pin for moving said lock pin away from said rotatable member, and a solenoid for driving said armature.

11. An X-ray source holding apparatus according to claim 10, wherein said unlock means further includes a rod-like link mechanism having a first end which is connected to said lock pin and a second end which is to be pushed by said solenoid, said link mechanism disengaging said lock pin from one of said positioning parts, to thereby allow the movement of said X-ray source, when said second end of said link mechanism is pushed by said solenoid.

12. An X-ray source holding apparatus according to claim 9, wherein said brake means includes an electromagnetic brake.

13. An X-ray source holding apparatus, comprising:
  a holding unit which movably holds an X-ray source;
  a lock mechanism for inhibiting the movement of said X-ray source;

a rod-like mechanism having a first end which is connected to said lock mechanism and a second end which is to be moved in a predetermined direction, said link mechanism disengaging said lock mechanism and one of positioning parts from each other, to thereby allow the movement of said X-ray source, when said second end of said link mechanism is moved in said predetermined direction;

unlock means for disengaging said lock mechanism so as to allow the movement of said X-ray source, said unlock means including: an armature having a tip end which is adapted to push said second end of said link mechanism; and a solenoid for moving said armature toward said second end of said link mechanism;

setting means for setting said armature at a position located away from said second end of said link mechanism; and control means for energizing said unlock means during a predetermined period of time upon reception of a command which is externally supplied.

14. An X-ray source holding apparatus according to claim 13, wherein:

said X-ray source is provided on a movable member having positioning parts;

said lock mechanism includes a lock pin engageable with one of said positioning parts, and a spring for urging said lock pin toward said movable member; and said unlock means drives said lock pin such that said lock pin is separated from one of said positioning parts against an urging force of said spring and is moved to said position where said armature is set by said setting means, thereby allowing the movement of said X-ray source.

15. An X-ray source holding apparatus according to claim 14, wherein said setting means includes a spring, said spring having a first end connected to said housing and a second end connected to said armature, and producing a shrinkage force weaker than a driving force with which said solenoid drives said armature.

16. An X-ray source holding apparatus according to claim 14, wherein said setting means includes a weight, said weight being connected to said armature through the medium of a wire and producing a attracting force weaker than a driving force with which said solenoid drives said armature.

17. An X-ray source holding apparatus according to claim 14, wherein said setting means supplies said solenoid with a current which flows in the polarity is different from polarity of a current which said solenoid is supplied when said armature is moved to said second end of said link mechanism.

18. An X-ray source holding apparatus according to claim 14, wherein said setting means includes a magnet facing said armature, said magnet producing a magnetic force weaker than a driving force with which said solenoid drives the armature.

19. An X-ray source holding apparatus according to claim 14, further comprising a brake means for locking said X-ray source at an arbitrary position thereof, said control means causing said brake means to unlock said X-ray source upon reception of a command which is externally supplied.

20. An X-ray source holding apparatus according to claim 19, wherein said brake means includes an electromagnetic brake.

* * * * *